(12) United States Patent
House

(10) Patent No.: US 8,491,552 B2
(45) Date of Patent: Jul. 23, 2013

(54) EXTERNAL CATHETER WITH ANTISEPTIC AGENT

(75) Inventor: Jamie Glen House, Colorado Springs, CO (US)

(73) Assignee: Adapta Medical, Inc., Colorado Springs, CO (US)

( * ) Notice: Subject to any disclaimer, the term of this patent is extended or adjusted under 35 U.S.C. 154(b) by 65 days.

(21) Appl. No.: 11/526,052

(22) Filed: Sep. 25, 2006

(65) Prior Publication Data

US 2008/0077099 A1    Mar. 27, 2008

(51) Int. Cl.
*A61F 5/44*    (2006.01)

(52) U.S. Cl.
USPC .......................................... 604/349; 604/355

(58) Field of Classification Search
USPC .................. 604/317, 327, 346, 347, 349–353, 604/355
See application file for complete search history.

(56) References Cited

U.S. PATENT DOCUMENTS

| | | | |
|---|---|---|---|
| 4,622,033 A | 11/1986 | Taniguchi | |
| 4,772,275 A | 9/1988 | Erlich | |
| 4,834,710 A | 5/1989 | Fleck | |
| 4,930,522 A * | 6/1990 | Busnel et al. | 128/844 |
| 5,149,326 A | 9/1992 | Woodgrift et al. | |
| 5,181,913 A | 1/1993 | Erlich | |
| 5,662,631 A * | 9/1997 | Marx | 604/352 |
| 5,779,670 A | 7/1998 | Bidwell et al. | |
| 5,792,114 A | 8/1998 | Fiore | |
| 5,827,247 A * | 10/1998 | Kay | 604/327 |
| 5,895,374 A | 4/1999 | Rodsten | |
| 6,007,526 A * | 12/1999 | Passalaqua et al. | 604/349 |
| 6,053,905 A | 4/2000 | Daignault et al. | |
| 6,059,107 A | 5/2000 | Nosted et al. | |
| 6,176,849 B1 | 1/2001 | Yang et al. | |
| 6,217,569 B1 | 4/2001 | Fiore | |
| 6,409,717 B1 | 6/2002 | Israelsson et al. | |
| 6,471,684 B2 | 10/2002 | Dulak et al. | |
| 6,551,293 B1 * | 4/2003 | Mitchell | 604/353 |
| 6,578,709 B1 | 6/2003 | Kavanagh et al. | |
| 6,589,544 B2 * | 7/2003 | Leong | 424/402 |
| 6,602,244 B2 | 8/2003 | Kavanagh et al. | |
| 6,634,498 B2 | 10/2003 | Kayerod et al. | |
| 6,673,053 B2 | 1/2004 | Wang et al. | |
| 6,699,226 B2 * | 3/2004 | Velazquez | 604/349 |
| 6,736,805 B2 | 5/2004 | Israelsson et al. | |
| 6,805,690 B2 * | 10/2004 | Ogden et al. | 604/352 |
| 6,848,574 B1 | 2/2005 | Israelsson et al. | |
| 2001/0001443 A1 | 5/2001 | Kayerod et al. | |
| 2001/0007060 A1 | 7/2001 | Fiore | |
| 2001/0027295 A1 | 10/2001 | Dulak et al. | |
| 2001/0027299 A1 | 10/2001 | Yang et al. | |
| 2003/0018302 A1 | 1/2003 | Kavanagh et al. | |
| 2004/0006321 A1 | 1/2004 | Cheng et al. | |
| 2004/0074794 A1 | 4/2004 | Conway et al. | |

(Continued)

*Primary Examiner* — Tatyana Zalukaeva
*Assistant Examiner* — Benedict L Hanrahan
(74) *Attorney, Agent, or Firm* — Moazzam & Associates, LLC.

(57) ABSTRACT

An external catheter device is disclosed which prevents infection arising from bacterial and/or yeast growth within the external catheter. To achieve such result, the external catheter device is coated with an antiseptic agent that is able to effectively kill and prevent the growth of bacteria and yeast. Additionally, the external catheter device may have an adhesive agent coating on its inner surface to prevent the condom from shifting while on the patient's penis.

12 Claims, 1 Drawing Sheet

U.S. PATENT DOCUMENTS

| | | |
|---|---|---|
| 2004/0087921 A1* | 5/2004 | Guldfeldt et al. ............. 604/349 |
| 2004/0153051 A1 | 8/2004 | Israelsson et al. |
| 2004/0210289 A1 | 10/2004 | Wang et al. |
| 2004/0256264 A1 | 12/2004 | Israelsson et al. |
| 2005/0015076 A1 | 1/2005 | Giebmeyer et al. |
| 2005/0109648 A1 | 5/2005 | Kerzman et al. |
| 2005/0137582 A1 | 6/2005 | Kull-Osterlin et al. |
| 2006/0025753 A1 | 2/2006 | Kubalak et al. |

* cited by examiner

EXTERNAL CATHETER WITH ANTISEPTIC AGENT

BACKGROUND OF THE INVENTION

1. Field of the Invention

The present invention relates generally to catheters. More particularly, the present invention relates to external catheters having antiseptic agents capable of killing and/or preventing the growth of bacteria and/or yeast.

2. Background of the Invention

In home and hospital settings, it is common practice to employ catheterization devices to drain urine from patients. Such catheterization devices include indwelling catheters, intermittent catheters, and external catheters, which are also known as condom catheters.

In patients with normal control over bladder functions, an external catheter is sometimes used instead of an indwelling or intermittent catheter since the risk of infection or other disease may be minimized with an external catheter. An external catheter is not inserted into the patient's urethra, and it therefore may have some advantages over other current catheterization devices that require temporary or prolonged urethral insertion in order to drain the urine from the bladder.

An external catheter is placed over a patient's penis like a condom used for sexual intercourse and has at its end a reservoir connected to a tube which is connected to a collection bag. Earlier external catheters were not self-adhesive and a band around the catheter was used to hold the catheters in place on the penis. Later advancements were made in the adhesive techniques which resulted in lining the inside of the catheter with a glue-like substance. This caused the condom-like catheter to stick to the flaccid penis and keep it in place throughout the day. Some also use a skin-prep pad that is wiped on the penis before the external catheter is applied which quickly turns into a sticky gel-like substance which further causes the catheter to stick to the penis. This pad is so sticky when first applied that it is difficult to remove without damaging the skin.

An external catheter is usually used on patients who have an ability to control their bladder functions but may have limited hand dexterity or ability to get to a toilet, or may be unable to direct their urine flow into a urinal. Also, an external catheter can be used on individuals having abnormal bladder function but who may still experience spontaneous bladder contraction after their bladder is full. This often occurs in patients with stroke, multiple sclerosis, spinal cord injury, traumatic brain injury, etc. An external catheter is not normally used for patients with bladders that are unable to contract, such as patients with spina bifida. External catheters have been mostly comprised of a latex material until recently when silicon catheters have become popular.

There are studies that have shown that the rate of urinary tract and bladder infection is lower for individuals who change their external condom catheter daily as compared to every other day. Therefore, most doctors recommend that an external catheter be changed every day to prevent infections. However, infections do still occur at a significant rate in those individuals who depend on external catheters due to the prolonged presence of residual urine within the tip of the external catheter.

Thus, there is a need in the healthcare industry for a catheterization device, specifically an external catheter, that functions effectively for a sustained period of time without being prone to infection.

SUMMARY OF THE INVENTION

The current techniques and devices for catheterization are inefficient and expose the patient to infection. In current external catheterization devices, residual urine collects in the reservoir of the catheter. Such residual urine can be associated with an increase in bacterial and/or yeast infection and may arise from the proliferation of skin bacteria and/or yeast within this urine medium. This collection of bacteria and/or yeast within the external catheter likely results in urinary tract and bladder infections by migration of these organisms retrograde through the urethra and into the bladder. These infections may still arise even if the external catheter is changed daily. In order to prevent this bacterial and/or yeast proliferation, the present invention proposes an antiseptic coating in at least the reservoir tip of the external catheter and an antiseptic coating in conjunction with an adhesive compound coating on the body of the external catheter that makes contact with at least the shaft of the penis.

In one exemplary embodiment, the present invention is an external catheterization device. The device includes an ensheathing condom; wherein the ensheathing condom contains an antiseptic agent on its interior surface.

In another exemplary embodiment, the present invention is an external catheterization device. The device includes an ensheathing condom having a body, an end surrounding the head of the penis, and a reservoir tip; wherein the ensheathing condom has on its inner surface an antiseptic agent.

In yet another exemplary embodiment, the present invention is an external catheterization device. The device includes an ensheathing condom having a body which extends over a shaft of a penis, an end surrounding a head of the penis, and a reservoir tip; a tube connecting end; and a tube connection port; wherein the body, the end, and the reservoir have on their inner surfaces an antiseptic agent coating; and wherein the tube connection port is used to empty urine from within the reservoir and the ensheathing condom.

In another exemplary embodiment, the present invention is an external catheterization device. The device includes an ensheathing condom having a body which extends over a shaft of the penis, an end surrounding a head of the penis, and a reservoir tip; a tube connecting end; and a tube connection port; wherein the body, the end, and the reservoir have on their inner surfaces an antiseptic agent coating formed from a group of agents selected from the following: nitrofurazone, chlorhexadine, silver sulfadiazine, minocycline, rifampin, nystatin, fluconazole, miconazole, troconazole, ibutoconazole, or any combination thereof; wherein the tube connection port is used to empty urine from within the reservoir and the ensheathing condom.

DETAILED DESCRIPTION OF THE INVENTION

The present invention provides for catheterization techniques and devices which prevent bacterial and/or yeast proliferation within the catheterization devices thereby preventing infection. In particular embodiments and examples presented herein, such catheters are described with respect to urinary catheterization but it must be noted that such antiseptic and adhesive compound coatings according to the present invention are not limited to urinary catheters alone but may be applicable to any catheterization device that could benefit from the use of such coatings.

Figure 1A:
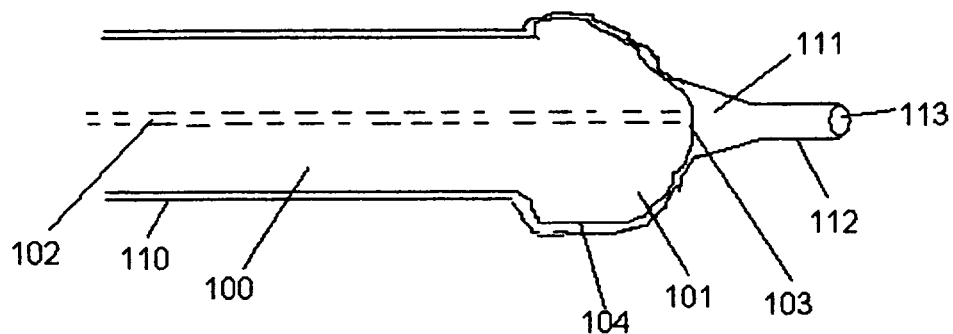
FIG. 1A shows a side view of a conventional external catheter without an antiseptic coating according to current catheterization techniques and devices.

A conventional external catheter 110 is shown in FIG. 1A. The external catheter 110 includes a reservoir tip 111 with a tube connecting end 112 and tube connection port 113. The external catheter 110 is condom-shaped and fits over the shaft 100 and head 101 of the patients penis. The external catheter 110 is conventionally composed of latex, rubber, silicon, or polyurethane. The external catheter 110 is tight fitting along the shaft 100 and on the head sides 104 of the penis in order to prevent leakage of urine (not shown) from the head tip 103 down the shaft 100 of the penis. In order to achieve this tight-fit, an adhesive glue-like material is conventionally used, such as an acrylic resin. The reservoir tip 111 is loosely fitting over the head tip 103 of the penis in order to allow for urine to collect and pass through the tube connecting end 112 and into a connecting tube (not shown).

Figure 1B:
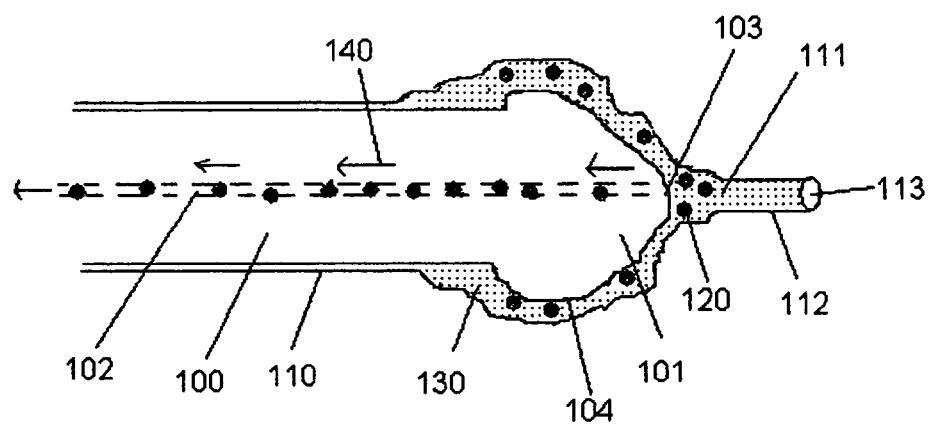
FIG. 1B shows a side view of a conventional external catheter without an antiseptic coating when residual urine collects within the catheter and when bacteria and/or yeast proliferate and travel up the patient's urethra.

During urination, urine 130 is collected within the reservoir tip 111 and allowed to pass through the tube connecting end 112 as shown in FIG. 1B. The accumulated urine 130 may travel down the shaft 100 of the penis as the reservoir tip 111 is expanded due to the pressure exerted by the accumulated urine 130 on the inside of the external catheter 110. This causes the external catheter to expand out from the penis head 101 as shown in FIG. 1B. As a result of this urine collection in the reservoir tip 111 and along the shaft 100 of the penis, not all of the accumulated urine 130 may drain out through the tube connecting end 112 and into the tube connection port 113. Thus, some residual urine may remain on the shaft 100, the head sides 101, and the head tip 103 after it is emptied out into a connecting tube (not shown) and into a collection bag (not shown). Such an accumulation of residual urine around these areas may result in the proliferation of bacteria or yeast 120. These bacteria or yeast 120 may originate from the normal epithelial cells on the penis and they may proliferate in the nutritive residual urine. Also, bacteria or yeast 120 may proliferate during the expected accumulation process of urine 130 within the external catheter 110 depending on how often the external catheter 110 is changed. Once the bacteria or yeast 120 are given a nutritive environment to proliferate (e.g., the urine 130), the bacteria or yeast may thereafter travel up the urethra 102 in the direction of arrows 140. Thus, the bacteria or yeast 120 can lead to a troublesome infection of the patient's bladder (not shown) and urethra 102.

Figure 2:
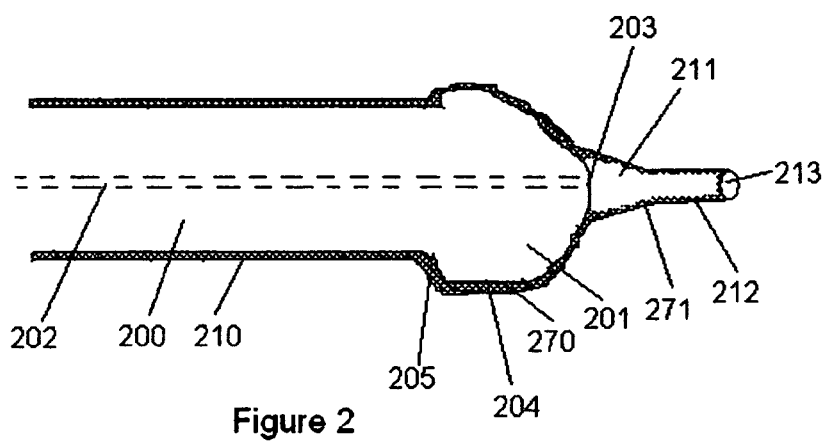
FIG. 2 shows a side view of an external catheter with an antiseptic coating and an adhesive compound coating on the inside body of the catheter that makes contact with at least the shaft of the penis while an antiseptic coating is used on at least the inside of the reservoir tip according to an exemplary embodiment of the present invention.

An exemplary embodiment of the present invention is external catheter 210 as shown in FIG. 2. External catheter 210 may include a reservoir tip 211, a tube connecting end 212, and a tube connection port 213 which may all be coated with an antiseptic agent 271 to prevent bacterial or yeast proliferation (not shown). External catheter 210 may also include an adhesive and antiseptic agent combination 270 coating the inner surface of the external catheter 210 at the shaft 200 in order to keep the external catheter 210 in place. The coating may also coat the inner surface of the external catheter at head sides 204 and just up to the head tip 203 as shown in FIG. 2. In this way, the external catheter 210 may be securely and tightly fitted to the shaft 200 and the head 201 of the penis in order to minimize any leakage of urine to these areas within the external catheter 210. As such, the adhesive and antiseptic agent combination 270 may cover the shaft 200 and the head 201 of the penis as shown in FIG. 2, or the adhesive and antiseptic combination 270 may not cover any portion of the head 201, and it may only cover the shaft 200 of the penis in order to avoid irritating the head 201 of the penis. In the latter case, the antiseptic agent 271 may coat both the inner surface of the reservoir tip 211 and the inner surface of the external catheter surrounding the head 201 of the penis by itself without any adhesive compound. Thus, the adhesive and antiseptic combination 270 may coat only the inner surface of the catheter surrounding the shaft 200 of the penis up until the base 205 of the head 201, and the antiseptic agent 271 may by itself coat the inner surface of the catheter surrounding the head 201 of the penis, the reservoir tip 211, and tube connecting end 212 and tube connection port 213 in order to minimize potential irritation to the head 201 of the penis. Both of the aforementioned variations involving the adhesive compound (e.g., whether or not it is on the head 101 of the penis) are within the scope of this invention so long as the external catheter 210 is able to remain securely fitted to the penis.

The antiseptic agent 271 may be composed of any anti-bacterial compound that effectively prevents the growth of bacteria (e.g., bacteriostatic) or yeast (e.g. anti-yeast) and/or kills bacteria (e.g., bacteriocidal) or yeast once they are formed. The antiseptic agent 271 should preferably be safe, non-irritating, and hypoallergenic such that it does not cause any adverse reactions to the skin of the patient. An exemplary anti-bacterial agent that may be used in the antiseptic agent for the present invention may be nitrofurazone, chlorhexadine, silver sulfadiazine, minocycline, rifampin, or any combination thereof. An exemplary anti-yeast agent that may be used in the antiseptic agent for the present invention may include, but not be limited to nystatin, fluconazole, miconazole, troconazole, ibutoconazole, or any combination thereof. These compounds have been effectively and safely used in Foley catheters (e.g., indwelling catheters) to prevent bacterial or yeast infection. Thus, a coating comprised of said compounds for the present invention may provide a safe and effective prevention of bacterial and/or yeast growth and subsequent infection. Alternatively, the antiseptic agent 271 may be pre-manufactured within the polymeric body of the catheter 210. Thus, the polymeric body of the catheter 210 itself would have antiseptic properties without the need to add a separate antiseptic agent at a later point after manufacture.

The adhesive material used for this invention may be composed of any compound that when applied to the inner surface of the catheter, may bind with the epithelial cells of the penis such that the catheter remains stable and secure on the shaft and head of the penis. The adhesive compound may also be non-irritating such that it may be removed from the penis without causing any irritation. The adhesive compound may be strong enough to resist any sliding movement of the catheter on the penis, but should preferably not be so strong so as to cause pain during removal of the catheter. An exemplary adhesive compound may be an acrylic resin as used in conventional catheters, but any other adhesive compound that would satisfy the above mentioned limitations would be suitable for use in the present invention as well.

The external catheter 210 may be composed of a material such that it may resist tearing during application, removal, and while the external catheter is fitted tightly around the penis. Also, the material composing the external catheter 210 may bind sufficiently to the adhesive and antiseptic agent combination 270, and the antiseptic agent 271 by itself such that said combination or agent by itself can stably reside on the inner surface of the external catheter while not sliding off the inner surface of the catheter or sliding down the catheter towards or away from the shaft 200 of the penis. In this way, the combination or agent by itself may remain on the inner surface of the external catheter 210 at specified areas including but not limited to the reservoir tip 211, head sides 204, and shaft 200 of the penis. Such a material for use in the external catheter 210 may include, but is not limited to, silicon, rubber, latex, polyurethane, or any combination thereof.

The manufacturing methods that can be employed for the present invention include, but are not limited to, conventional techniques used in the industry to produce similar function products, as known by a person having ordinary skill in the art.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. An external catheterization device, the device comprising:
    an ensheathing condom having a first portion adapted for surrounding a shaft of a penis, and a second portion adapted for surrounding a head of the penis;
    wherein the ensheathing condom contains a combination of an antiseptic agent and an adhesive agent on a first interior surface of the first portion, and the antiseptic agent on a second interior surface of the second portion for surrounding a head of the penis,
    wherein the antiseptic agent contains an anti-bacterial compound to prevent bacterial proliferation due to accumulated residual urine, the anti-bacterial compound including chlorhexidine,
    wherein the adhesive compound keeps the ensheathing condom in place as the first interior surface of the first portion of the ensheathing condom fits tightly around the shaft of the penis, and
    wherein the adhesive compound on the first interior surface binds with an epithelial layer of the shaft of the penis and with the first interior surface such that only the second interior surface without the adhesive comes into contact with the head of the penis.

2. The device of claim 1, wherein the anti-bacterial compound further includes nitrofurazone, silver sulfadiazine, minocycline, rifampin, or any combination thereof.

3. The device of claim 1, wherein the anti-yeast compound is composed of nystatin, fluconazole, miconazole, troconazole, ibutoconazole, or any combination thereof.

4. The device of claim 1, wherein the ensheathing condom is further comprised of an end surrounding the head of the penis and a reservoir tip for urine collection.

5. The device of claim 1, further including a connection port for directing urine out of the ensheathing condom.

6. An external catheterization device, the device comprising:
    an ensheathing condom having a body adapted for surrounding a shaft of a penis, an end adapted for surrounding a head of the penis, and a reservoir tip, an adhesive agent combined with an antiseptic agent applied on a first inner surface of the body, and the antiseptic agent applied on a second inner surface of the end;
    wherein the ensheathing condom is fitted over the penis such that the antiseptic agent is initially in contact with the penis and remains in contact with the penis during use, the antiseptic agent containing an anti-bacterial compound to prevent bacterial proliferation due to accumulated residual urine, the anti-bacterial compound including chlorhexidine, and
    wherein the adhesive compound on the first inner surface of the body binds with an epithelial layer of the shaft of the penis and with the first inner surface such that only the second interior surface without the adhesive comes into contact with the head of the penis.

7. The device of claim 6, wherein the anti-bacterial compound further comprises nitrofurazone, silver sulfadiazine, minocycline, rifampin, or any combination thereof 8. The device of claim 6, wherein the anti-yeast compound is composed of nystatin, fluconazole, miconazole, troconazole, ibutoconazole, or any combination thereof.

9. The device of claim 6, further including a connection port for directing urine out of the ensheathing condom.

10. An external catheterization device, the device comprising:
    an ensheathing condom having a body which extends over a shaft of a penis, an end surrounding a head of the penis, and a reservoir tip;
    a tube connecting end; and
    a tube connection port;
    wherein the body, the end, and the reservoir have on their interior surfaces an antiseptic agent coating, the interior surfaces in contact with the penis during use, the antiseptic agent containing an anti-bacterial and anti-yeast compound to prevent bacterial and yeast proliferation due to accumulated residual urine, the anti-bacterial compound including chlorhexidine and being initially in contact with the penis when the ensheathing condom is fitted over the penis,
    wherein the body further includes an adhesive agent combined with the antiseptic agent on a first interior surface of the body, the adhesive compound binding with an epithelial layer of the shaft of the penis and with the first interior surface such that the adhesive agent does not come into contact with the head of the penis; and
    wherein the tube connection port is used to empty urine from within the reservoir and the ensheathing condom.

11. The device of claim 10, wherein the anti-bacterial compound further comprises nitrofurazone, silver sulfadiazine, minocycline, rifampin, or any combination thereof.

12. The device of claim 10, wherein the anti-yeast compound is composed of nystatin, fluconazole, miconazole, troconazole, ibutoconazole, or any combination thereof.

* * * * *